United States Patent
Akiyama et al.

(10) Patent No.: US 6,242,008 B1
(45) Date of Patent: *Jun. 5, 2001

(54) SPHERICAL PHARMACEUTICAL GRANULES COMPRISING MICROCRYSTALLINE CELLULOSE AND A PROCESS FOR THEIR PRODUCTION

(75) Inventors: Hidero Akiyama, Tokyo; Zene Matsumoto; Takashi Ueno, both of Gunma, all of (JP)

(73) Assignee: SmithKline Beecham Seiyaku K.K., Gumma (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,948
(22) PCT Filed: Sep. 4, 1996
(86) PCT No.: PCT/JP96/02504
  § 371 Date: Jul. 7, 1998
  § 102(e) Date: Jul. 7, 1998
(87) PCT Pub. No.: WO97/10810
  PCT Pub. Date: Mar. 27, 1997

(30) Foreign Application Priority Data
  Sep. 9, 1995 (GB) .................................................. 9518465

(51) Int. Cl.⁷ ................................ A61K 9/14; A61K 9/16
(52) U.S. Cl. .......................... 424/490; 424/489; 514/262; 514/951
(58) Field of Search .................................... 424/489, 494, 424/490; 514/951, 262

(56) References Cited

U.S. PATENT DOCUMENTS

| | | | |
|---|---|---|---|
| 4,948,589 | * | 8/1990 | Iijima et al. |
| 5,262,173 | * | 11/1993 | Sheth et al. |
| 5,292,461 | | 3/1994 | Juch et al. ............................. 264/37 |
| 5,998,605 | * | 12/1999 | Chamberlain et al. |

FOREIGN PATENT DOCUMENTS

| | | |
|---|---|---|
| 0 608 850 | 8/1994 | (EP). |
| 6-211515 | * 8/1994 | (JP). |

OTHER PUBLICATIONS

Vertommen et al., European Journal of Pharmaceutics, 40(1), pp. 32–35 (1994), 2/94.

* cited by examiner

Primary Examiner—Thurman K. Page
Assistant Examiner—Brian K. Seidleck
(74) Attorney, Agent, or Firm—Dara L. Dinner; Stephen Venetianer; Charles M. Kinzig (57) ABSTRACT

A high speed agitation granulator method of preparing a substantially spherical granule for pharmaceutical use comprising a medicament for pharmaceutical use, wherein the medicament has an aqueous solubility of 0.01 to 0.30 g/ml, which method comprises introducing a mixture of medicament and excipients comprising at least 5% crystalline cellulose into the granulator and spraying on water or a mixture of ethanol and water as binder solution; a substantially spherical granule for pharmaceutical use comprising famciclovir and 5% or more crystalline cellulose, together with an optional coating; and a sachet containing a unit dose of famciclovir in the form of such granules.

10 Claims, 7 Drawing Sheets

Fig.1

Microscopic Photos of Pyridoxine Spherical Granules (A) Binder Solution: Water, X5.

(A)

1000 μm

Microscopic Photos of Pyridoxine Spherical Granules (B) Binder Solution: 70% Ethanol, X5.

Microscopic Photos of Pyridoxine Spherical Granules (A) Concentration of Microcrystalline Cellulose: 20%, X5.

Microscopic Photos of Pyridoxine Spherical Granules (B) Concentration of Microcrystalline Cellulose: 75%, X5.

Fig. 3. Relationship between Amount of Binder Solution and D50% of Pyridoxine Spherical Granules Fig. 4. Relationship between Agitation Time of Blade/Cross screw and Shape Factor of Pyridoxine Spherical Granules
◇, SF1;  ○, SF2.

Fig.5

Microscopic Photos of Pyridoxine Spherical Granules (A) Stirring Time: 0 Min, X5.

Microscopic Photos of Pyridoxine Spherical Granules (B-1) Stirring Time: 14 Min, X5.

Fig.5

Microscopic Photos of Pyridoxine Spherical Granules

(B-2) Stirring Time: 14 Min, X15.

1000 μm

Microscopic Photos of Pyridoxine Spherical Granules (C) Stirring Time: 30 Min, X5.

1000 μm

Fig. 6. Dissolution Curve of Pyridoxine Spherical Granules

Fig.7

Microscopic Photos of Pyridoxine Spherical Granules
after Dissolution Test, X10

1000 μm

SPHERICAL PHARMACEUTICAL GRANULES COMPRISING MICROCRYSTALLINE CELLULOSE AND A PROCESS FOR THEIR PRODUCTION

This application is a 371 of PCT/JP96/02504, filed Sep. 4, 1996.

FIELD OF THE INVENTION

This invention relates to a method of preparation of granules incorporating a medicament for pharmaceutical use.

BACKGROUND OF THE INVENTION

Granules are a suitable form for medicaments which are to be administered orally. A dose of medicament in the form of granules may be measured and administered by incorporating into a sachet or using a spoon or may be incorporated into a capsule of formulated into a tablet to be swallowed. It is preferred that such granules are of regular shape and substantially spherical to give good fluidity for ease of dispensing and capsule filling or tabletting as well as for aesthetic appeal. Spherical granules are also easier to coat with taste masking, enteric/protective and sustained release coating materials.

At present, there are two methods of preparing spherical granules. One is to extrude a cylindrical granule using a "squeeze-out" type granulation machine and then to make it spherical in shape by using a marumeriser, a machine which "cuts off the edges" of the cylinder shape. This method involves difficult manufacturing conditions and is time consuming which precludes its routine use. The other method used is to gradually coat a core particle such as granulated sugar using a centrifugal flow type granulator but this is a time consuming process and is not generally applicable to a wide range of medicaments where the proportion of the volume of the medicament in the granules high (20% or higher).

The most efficient method of preparing granules is using a high-speed agitation granulator machine which mixes and granulates in one operation using two rotating blades, a main blade with a horizontal plane of rotation and a chopper blade above it with a vertical plane of rotation (cross blade). The medicament and excipients are introduced into the machine in advance and binder solution is then poured or sprayed into the machine from above whilst the blades are rotating. By this method, granules can be prepared quickly and easily but the disadvantage is that the resulting granules are irregular and non-spherical in shape and do not have the advantages associated with spherical granules.

Surprisingly, we have now discovered a method of preparing substantially spherical granules using a high-speed agitation granulator machine thus avoiding the need to use the "squeeze-out" and marumerizer method.

DETAILED DESCRIPTION OF THE INVENTION

Accordingly, the present invention provides a high speed agitation granulator method of preparing a substantially spherical granule for pharmaceutical use comprising a medicament for pharmaceutical use wherein the medicament has an aqueous solubility of 0.01 to 0.30 g/ml, which method comprises introducing a mixture of the medicament and excipients comprising at least 5% crystalline cellulose into the granulator and spraying on water or a mixture of ethanol and water as binder solution.

Suitable medicaments include caffeine which has an aqueous solubility 0.02 g/ml, pyridoxine hydrochloride which has an aqueous solubility of 0.22 g/ml and particularly the orally administered antiviral compounds, famciclovir and acyclovir which have a aqueous solubility of more than 0.25 g/ml. Generally the proportion of medicament with respect to excipients in the composition of the granule is up to 25%, such as up to 5%, 10%, 20%, although it is envisaged that up to 55% medicament could be incorporated.

The mixture of medicament and excipients comprise at least 5% crystalline cellulose, for example up to 10%, 20%, 30%, 40%, 50%, 60%, 70%, 80% and 90%. Other suitable additional excipients include lactose, although the highest yield of spherical granules are when the mixture contains crystalline cellulose as the sole excipient, for example where the composition contains 25% medicament and 75% crystalline cellulose.

The binder solution may be up to 75% ethanol and it is found that the sphericity of granules is higher when the ethanol concentration is higher although from a manufacturing environment point of view and to avoid any problems resulting from residual organic solvent, it may be preferable to use pure water as the binder solution. A linear relationship between the granule size and the amount of binder solution was observed such that the granule size can be regulated by this method (the greater the amount of binder solution, the larger the granule). The granules suitable for administration by spoon are generally more than 500 um in diameter, favourably more than 700 um, up to 1500 um, favourably up to 1000 um. Granules suitable for capsules or tablets are usually smaller than 500 um.

The granules are suitably agitated in the granulator after spraying of the binder solution to improve the spherical shape and smooth the surface of the granules. The agitation time will depend on the size of the granules and composition of the granules, together with the size of the granulator and the speed of rotation of the main blade and the cross blade. The agitation times generally range from 2 to 30 minutes.

The invention provides, in one aspect, a substantially spherical granule for pharmaceutical use comprising famciclovir and 5% or more crystalline cellulose, together with an optional coating. In a preferred aspect the invention provides such a granule comprising famciclovir and crystalline cellulose as the sole excipient, for example a granule containing 25% famciclovir and 75% cellulose.

The following Examples illustrate the process of the invention. The accompanying Figures and Tables illustrate the following with respect to pyridoxine granules:

BRIEF DESCRIPTION OF THE DRAWINGS

FIGS. 5 (A), (B-1), and (C) show photographs of granules taken through a microscope (×5) where agitation times are 0, 14 and 30 minutes respectively. FIG. 5 (B-2) shows a photograph of granules taken through a microscope (15) where the agitation time is 14 minutes.

Figure 1:
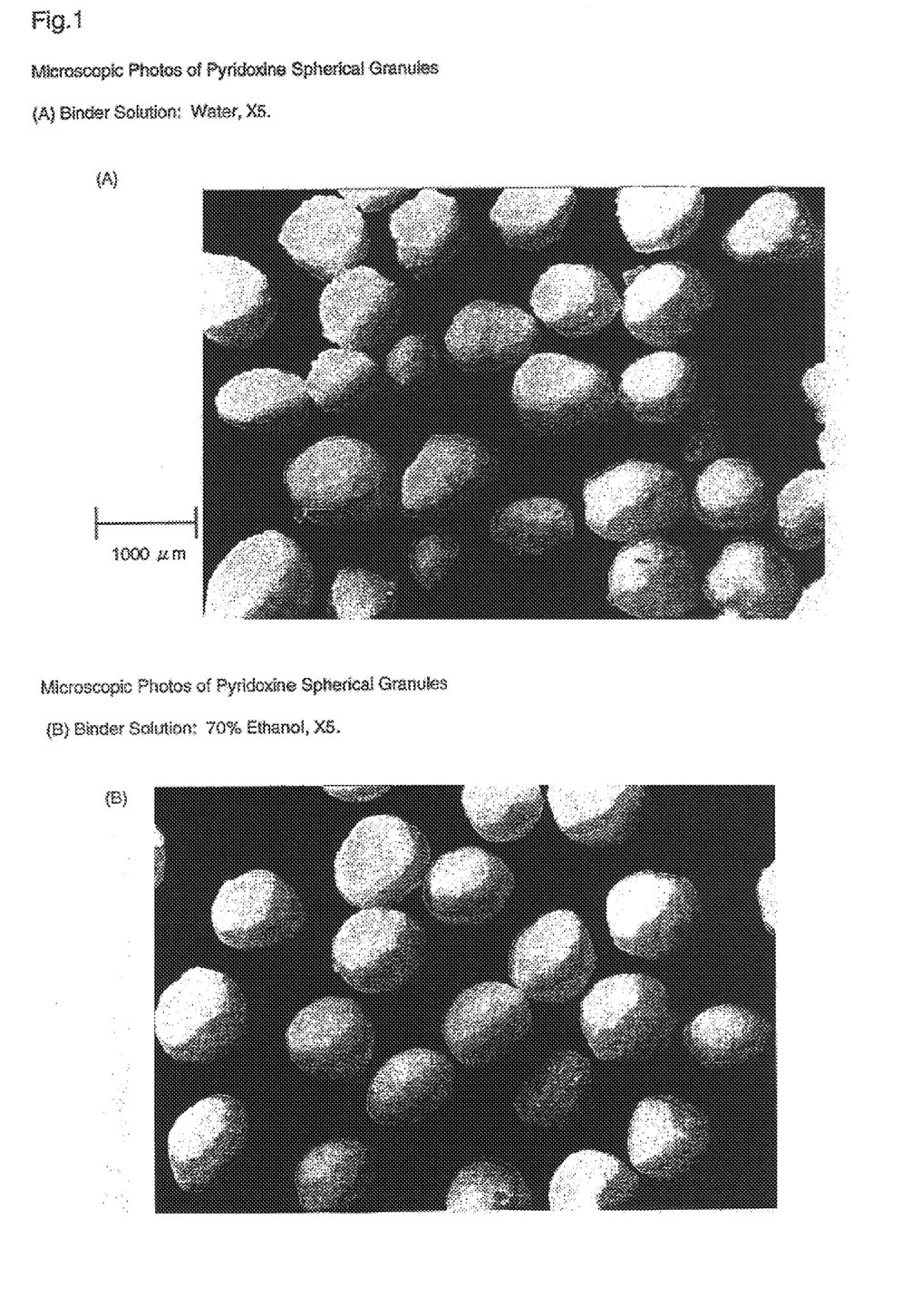
FIG. 1 shows photographs of granules taken through a microscope (×5). (A) is where the binder solution is water and (B) is where the binder solution is 70% ethanol.
Figure 2:
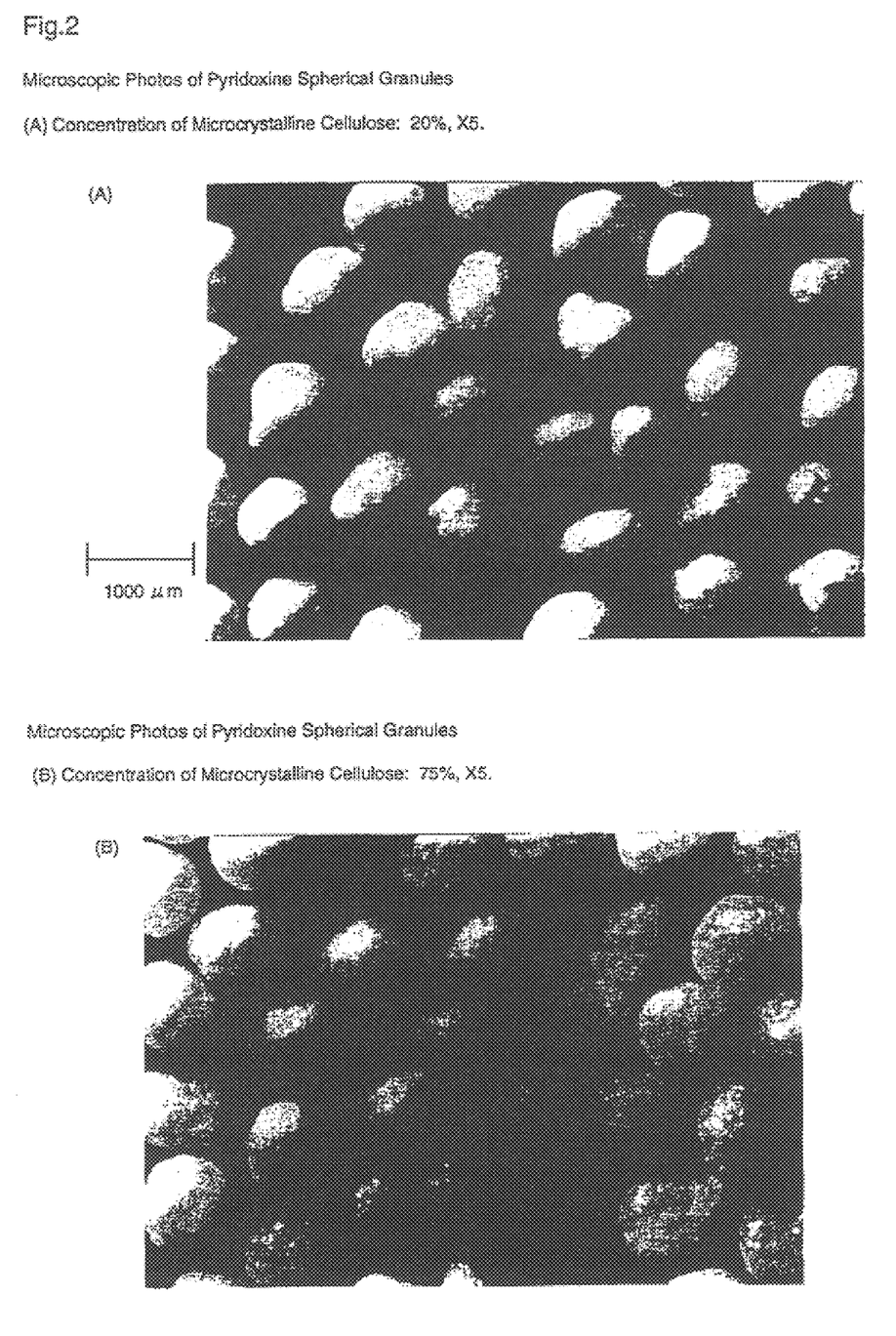
FIG. 2 shows photographs of granules taken through a microscope (×5). (A) is with 20% crystalline cellulose and (B) is with 75% crystalline cellulose.
Figure 3:
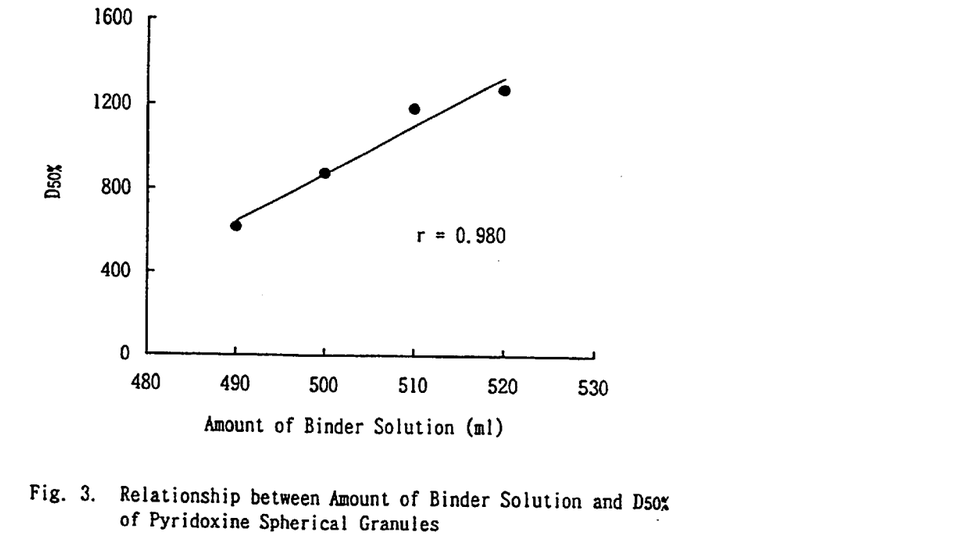
FIG. 3 is a graph showing the relationship between amount of binder solution and the size of granules.
Figure 4:
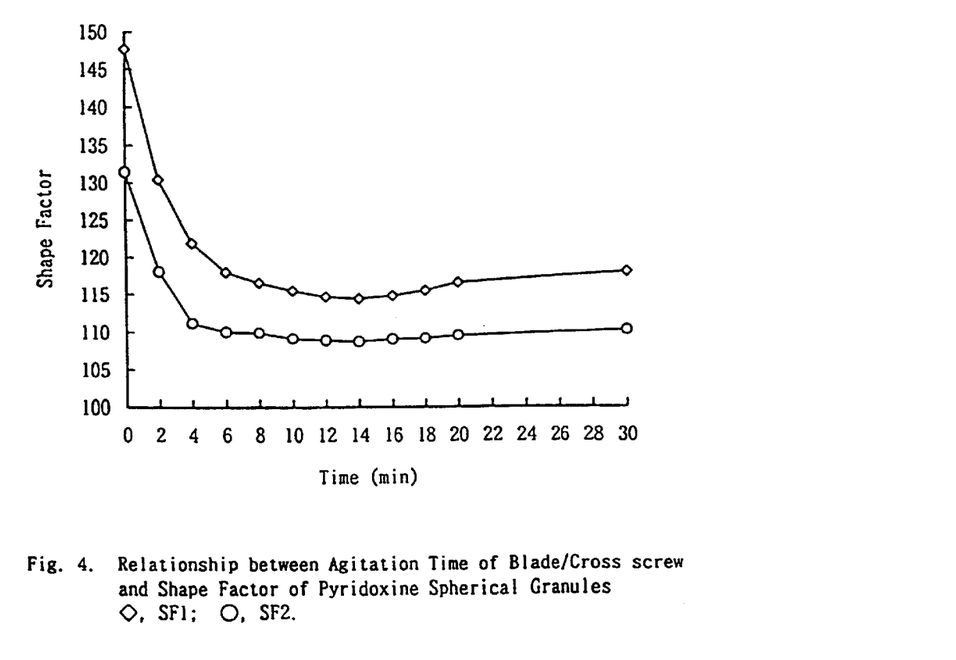
FIG. 4 is a graph showing the relationship between agitation time of the main and cross blades with respect to the shape factor of granules.
Figure 5:
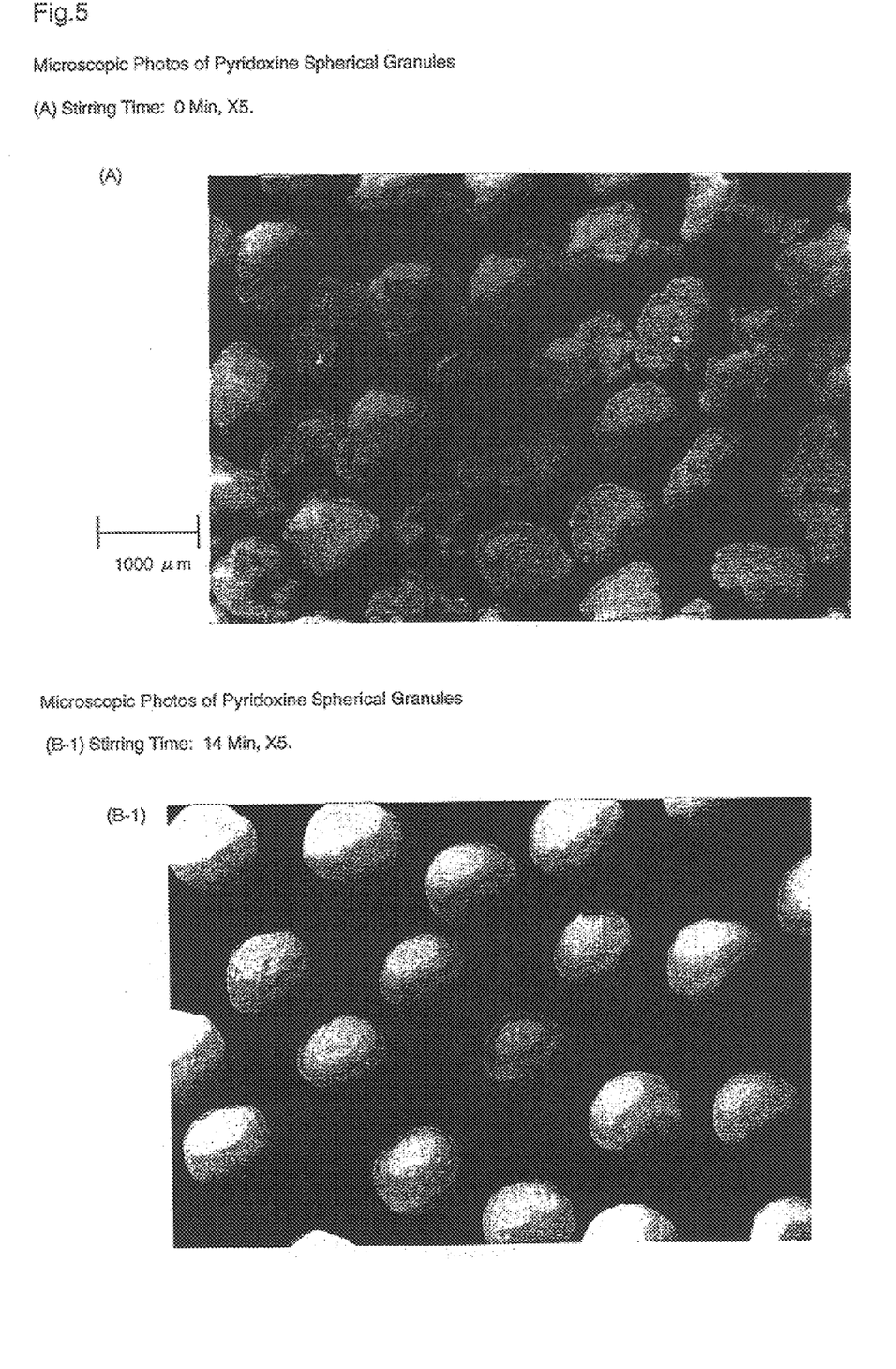
Figure 6:
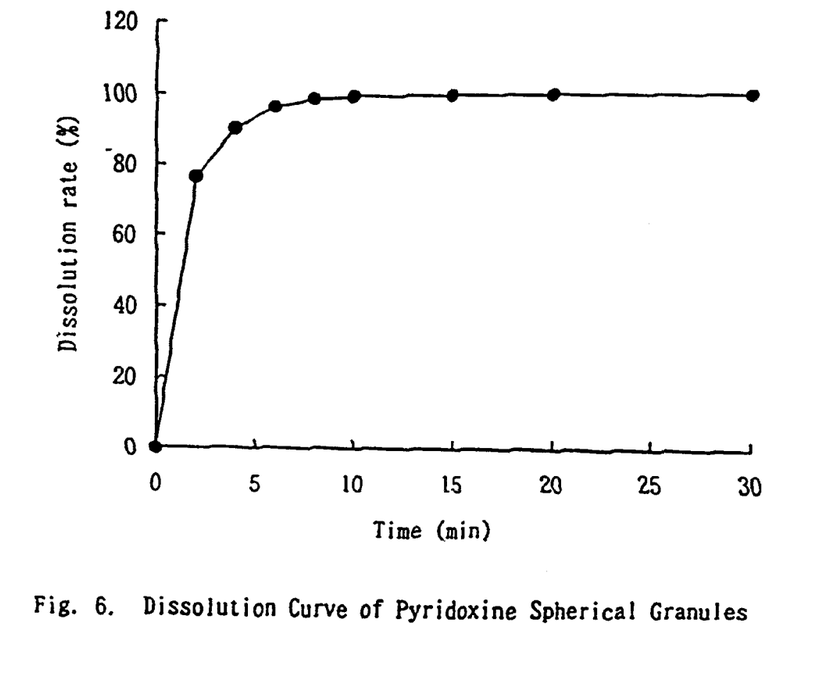
FIG. 6 is a graph shows the dissolution curve of the granules.
Figure 7:
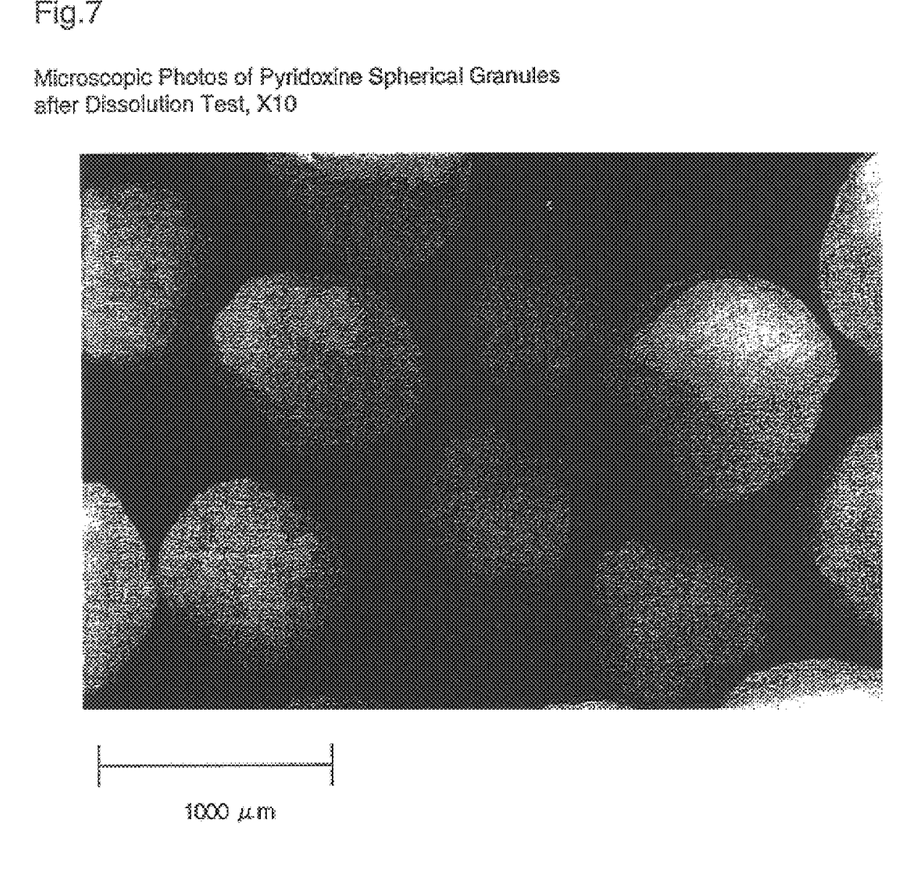
FIG. 7 shows a photograph of granules taken through a microscope (×10) after the dissolution test.

Table I shows the various compositions of the granules with respect to crystalline cellulose content.

Table II shows the effect of ethanol concentration in the binder solution on Shape Factor and yield of granules.

Table III shows the effect of microcrystalline cellulose concentration on Shape Factor and yield of granules.

Table IV shows the effect of amount of binder solution on Particle Size Distribution of 25% pyridoxine granules.

Table V shows the reproducibility of Shape Factor of 25% pyridoxine granules.

Table VI shows the reproducibility of Particle Size Distribution and yield of 25% pyridoxine granules.

EXAMPLES

Preparation Example 1

(10% Caffeine Spherical Granule)

In this example, 700 g of a mixture having the composition shown below were first charged into an agitation granulator (Type VG-5, manufactured by Powlex Corp., Japan) and then 180 ml of 20% ethanol-water solution as a binder liquid were sprayed, at a rate of 100 ml/min, over the mixture in the granulator while rotating the main blade and the cross blade of the granulator at 600 and 3000 rpm, respectively. After the end of spraying, the granulating operation was continued for another two minutes. The resulting grain was then dried at 50° C. for 12 hours using a convection drying oven to obtain the spherical granule.

| Composition of the mixture: | |
| --- | --- |
| Caffeine | 10 parts |
| Lactose | 82 parts |
| Crystalline cellulose | 8 parts |

The particle size of this spherical granule obtained was 500–850 um with a yield of 85.5%.

Preparation Example 2

(25% Caffeine Spherical Granule)

In this example, 700 g of a mixture having the composition shown below were first charged into an agitation granulator (Type VG-5, manufactured by Powlex Corp., Japan) and then 370 ml of 70% ethanol-water solution as a binder liquid were sprayed, at a rate of 100 ml/min, over the mixture in the granulator while rotating the main blade and the cross blade of the granulator at 600 and 3000 rpm, respectively. After the end of spraying, the granulating operation was continued for another five minutes while rotating the main blade and the cross blade at 300 and 1000 rpm, respectively. The resulting grain was then dried at 50° C. for 12 hours using a convection drying oven to obtain the spherical granule.

| Composition of the mixture: | |
| --- | --- |
| Caffeine | 25 parts |
| Lactose | 55 parts |
| Crystalline cellulose | 20 parts |

The particle size of this spherical granule obtained was 710–1180 um with a yield of 77.7%.

Preparation Example 3

(25% Pyridoxine Hydrochloride Spherical Granule)

In this example, 500 g of a mixture having the composition shown below were first charged into an agitation granulator (Type VG-5, manufactured by Powlex Corp., Japan) and then 350 ml of water as a binder liquid were sprayed, at a rate of 100 ml/min, over the mixture in the granulator while rotating the main blade and the cross blade of the granulator at 600 and 3000 rpm, respectively. After completing the spraying, the granulating operation was continued for another 14 minutes while rotating the main blade and the cross blade at 300 and 1000 rpm, respectively. The resulting grain was then dried at 50° C. for 12 hours using a convection drying oven to obtain the spherical granule.

| Composition of the mixture: | |
| --- | --- |
| Pyridoxine hydrochloride | 25 parts |
| Crystalline cellulose | 75 parts |

The particle size of this spherical granule obtained was 710–1180 um with a yield of 96.4%.

Preparation Example 4

(25% Famciclovir Spherical Granule)

In this example, 500 g of a mixture having the composition shown below were first charged into an agitation granulator (Type VG-5, manufactured by Powlex Corp., Japan) and then 458 or 459 ml of water as a binder liquid were sprayed, at a rate of 65 ml/min, over the mixture in the granulator while rotating the main blade and the cross blade of the granulator at 600 and 3000 rpm, respectively. After completing the spraying, the granulating operation was continued for another 30 minutes while rotating the main blade and the cross blade at 300 and 1000 rpm, respectively. The resulting grain was then dried at 50° C. for 12 hours using a convection drying oven to obtain the spherical granule.

| Composition of the mixture: | |
| --- | --- |
| Famciclovir | 25 parts |
| Crystalline cellulose | 75 parts |

Using 458 ml of binder solution, the particle size of the spherical granule obtained was 600–850 um with a yield of 97.1 percent. Using 459 ml of binder solution, the particle size of the spherical granule obtained was 710–1000 um with a yield of 97.0 percent.

Preparation Example 5
(25% Pyridoxine Hydrochloride Spherical Granule)

In this example, 500 g of a mixture having the composition shown below were first charged into an agitation granulator (Type VG-5, manufactured by Powlex Corp., Japan) and then 326 ml of water as a binder liquid were sprayed, at a rate of 80 ml/min, over the mixture in the granulator while rotating the main blade and the cross blade of the granulator at 600 and 3000 rpm, respectively. After completing the spraying, the granulating operation was continued for another 30 minutes while rotating the main blade and the cross blade at 400 and 2000 rpm, respectively. The resulting grain was then dried at 50° C. for 12 hours using a convection drying oven to obtain the spherical granule.

| Composition of the mixture: | |
|---|---|
| Pyridoxine hydrochloride | 25 parts |
| Crystalline cellulose | 75 parts |

The particle size of this spherical granule obtained was 300–500 um with a yield of 90.7%.

TABLE I

Formulas of Pyridoxine Spherical Granules(%)

| Formulation No. | PSG-1 | PSG-2 | PSG-3 | PSG-4 | PSG-5 | PSG-6 | PSG-7 | PSG-8 |
|---|---|---|---|---|---|---|---|---|
| Pyridoxine hydrochloride | 25 | 25 | 25 | 25 | 25 | 25 | 25 | 25 |
| Microcrystalline cellulose | 10 | 20 | 30 | 40 | 50 | 60 | 70 | 75 |
| Lactose | 65 | 55 | 45 | 35 | 25 | 15 | 5 | 0 |

TABLE II

Effect of Ethanol Concentration in the binder solution on Shape Factor and Yield of Pyridoxine Spherical Granules

| Ethanol concentration (%) | Shape Factor SF1 | Shape Factor SF2 | Yield (%) |
|---|---|---|---|
| 0 | 124.4 | 111.1 | 88.9 |
| 10 | 120.3 | 111.3 | 85.3 |
| 30 | 119.5 | 110.3 | 85.6 |
| 50 | 118.6 | 109.7 | 89.4 |
| 70 | 117.1 | 109.0 | 85.0 |

TABLE III

Effect of microcrystalline Cellulose Concentration on Shape Factor and Yield of Pyridoxine Spherical Granules

| Concentration of microcrystalline cellulose (%) | Shape Factor SF1 | Shape Factor SF2 | Yield (%) |
|---|---|---|---|
| 10 | 120.6 | 111.1 | 70.3 |
| 20 | 119.5 | 109.8 | 79.3 |
| 30 | 119.7 | 110.1 | 83.7 |
| 40 | 119.4 | 109.6 | 84.5 |
| 50 | 119.1 | 111.8 | 88.9 |
| 60 | 117.3 | 109.4 | 94.3 |
| 70 | 115.9 | 109.9 | 95.8 |
| 75 | 115.6 | 109.5 | 96.6 |

TABLE IV

Effect of Amount of Binder Solution on Particle Size Distribution of 25% Pyridoxine Spherical Granules

| Particle size ($\mu$m) | Amount of binder solution (ml) | | | |
|---|---|---|---|---|
| | 490 | 500 | 510 | 520 |
| 1400–1700 | 0.3% | 0.5% | 0.9% | 1.5% |
| 1180–1400 | 0.5 | 1.5 | 49.0 | 82.4 |
| 1000–1180 | 1.1 | 11.9 | 42.5 | 12.3 |
| 850–1000 | 1.9 | 74.0 | 5.9 | 2.5 |
| 710–850 | 7.5 | 10.6 | 1.1 | 0.6 |

TABLE IV-continued

Effect of Amount of Binder Solution on Particle Size Distribution of 25% Pyridoxine Spherical Granules

| Particle size ($\mu$m) | Amount of binder solution (ml) | | | |
|---|---|---|---|---|
| | 490 | 500 | 510 | 520 |
| 500–710 | 87.7 | 1.3 | 0.4 | 0.3 |
| 355–500 | 0.8 | 0.1 | 0.1 | 0.1 |
| 0–355 | 0.2 | 0.1 | 0.1 | 0.3 |
| D50% | 617 $\mu$m | 875 $\mu$m | 1180 $\mu$m | 1270 $\mu$m |

TABLE V

Reproducibility of Shape Factor of 25% Pyridoxine Spherical Granules

| Repetition No. | SF1 | SF2 |
|---|---|---|
| 1 | 114.1 | 108.2 |
| 2 | 114.3 | 108.0 |
| 3 | 114.2 | 107.9 |

TABLE V-continued

Reproducibility of Shape Factor of 25% Pyridoxine Spherical Granules

| Repetition No. | SF1 | SF2 |
|---|---|---|
| 4 | 114.4 | 108.2 |

TABLE VI

Reproducibility of Particle Size Distribution and Yield of 25% Pyridoxine Spherical Granules

| Particle size | Repetition No. | | | |
|---|---|---|---|---|
| ($\mu$m) | No. 1 | No. 2 | No. 3 | No. 4 |
| 1400–1700 | 0.9 | 0.2 | 0.2 | 0.4 |
| 1180–1400 | 1.8 | 1.0 | 1.0 | 1.6 |
| 1000–1180 | 5.8 | 4.1 | 3.4 | 3.5 |
| 850–1000 | 61.7 | 67.4 | 61.5 | 66.3 |
| 710–850 | 27.7 | 24.9 | 30.8 | 25.7 |
| 500–710 | 2.1 | 2.1 | 2.9 | 2.1 |
| 355–500 | 0.0 | 0.2 | 0.1 | 0.4 |
| 0–355 | 0.0 | 0.0 | 0.1 | 0.0 |
| Yield (710–1180) | 95.2 | 96.4 | 95.7 | 95.5 |

What is claimed is:

1. A method of preparing a substantially spherical granule of famciclovir, which method comprises introducing a mixture consisting essentially of approximately 25% famciclovir and 75% microcrystalline cellulose into a high speed agitation granulator and spraying on water or a mixture of ethanol and water as binder solution.

2. A method according to claim 1 where the amount of binder solution is regulated such that granules are suitable for administration by spoon and are generally more than 500 um in diameter.

3. A method according to claim 1 wherein the granules are agitated in the granulator after spraying of the binder solution to improve the spherical shape and smooth the surface of the granules.

4. A method according to claim 1 wherein the substantially spherical granule contains an optional coating.

5. A pharmaceutical composition of substantially spherical granules of famciclovir the granules consisting essentially of approximately 25% famciclovir and at least approximately 75% microcrystalline cellulose as the sole solid excipient wherein the spherical granules are produced in a high speed agitation granulator.

6. A method according to claim 1 or 4 wherein the microcrystalline cellulose is the sole excipient.

7. A granule according to claim 6 having a diameter of 500 to 1500 um.

8. A sachet containing a unit dose of famciclovir in the form of granules as defined in claim 5.

9. A method according to claim 1 wherein the granules have a diameter of between 500 and 1500um.

10. A composition according to claim 5 wherein the granules are optionally coated.

* * * * *

UNITED STATES PATENT AND TRADEMARK OFFICE
CERTIFICATE OF CORRECTION

PATENT NO. : 6,242,008 B1
DATED : June 5, 2001
INVENTOR(S) : Akiyama et al.

It is certified that error appears in the above-identified patent and that said Letters Patent is hereby corrected as shown below:

<u>Column 8,</u>
Line 21, should read:

-- 7. A granule according to claim 5 having a diameter of 500 to 1500 um. --.

Signed and Sealed this

Sixteenth Day of July, 2002

Attest:

Attesting Officer

JAMES E. ROGAN
*Director of the United States Patent and Trademark Office*